United States Patent
Lee et al.

(10) Patent No.: US 8,815,221 B2
(45) Date of Patent: Aug. 26, 2014

(54) COMPOSITION USED FOR SKIN WHITENING, PLANT EXTRACTED SKIN WHITENING COMPOSITION AND COMPOSITION HAVING A SKIN WHITENING EFFECT

(75) Inventors: Lain-Tze Lee, Hsinchu (TW); Hui-Ping Tsai, Hsinchu (TW); Ling-Meei Tsay, Taichung (TW); Li-Syuan Jian, Tainan (TW); Chia-Mu Tu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 465 days.

(21) Appl. No.: 12/850,672

(22) Filed: Aug. 5, 2010

(65) Prior Publication Data
US 2011/0033403 A1 Feb. 10, 2011

(30) Foreign Application Priority Data

Aug. 6, 2009 (TW) ............................... 98126506 A

(51) Int. Cl.
*A61K 8/00* (2006.01)
*A61Q 19/02* (2006.01)
*A61K 8/42* (2006.01)
*A61K 8/97* (2006.01)

(52) U.S. Cl.
CPC . *A61Q 19/02* (2013.01); *A61K 8/42* (2013.01); *A61K 8/97* (2013.01)
USPC .......................................... 424/62; 424/70.17

(58) Field of Classification Search
CPC ............ A61K 8/97; A61K 8/42; A61Q 19/02
See application file for complete search history.

(56) References Cited

FOREIGN PATENT DOCUMENTS

| CN | 1203804 A | 1/1999 | | |
|---|---|---|---|---|
| CN | 1235037 A | 11/1999 | | |
| CN | 1273103 A | 11/2000 | | |
| CN | 1583020 A | 2/2005 | | |
| CN | 101856346 A | 10/2010 | | |
| JP | 60-190713 A | 9/1985 | | |
| JP | 62-56459 A | 3/1987 | | |
| JP | 63-39847 A | 2/1988 | | |
| JP | 4-247012 A | 9/1992 | | |
| JP | 2004-175778 A | 6/2004 | | |
| JP | 2004-231558 A | 8/2004 | | |
| JP | 2004231558 | * | 8/2004 | ............. A61K 36/18 |
| KR | 10-0828193 A | * | 5/2008 | ............. A61K 36/62 |
| KR | 10-0828193 A | | 5/2008 | |

OTHER PUBLICATIONS

Bokern, M. et al, "Trisubstituted Hydroxycinnamic Acid Spermidines From *Quercus dentata* Pollen," Phytochemistry, 1995, vol. 39, No. 6, pp. 1371-1375.

Chinese Office Action, Appl. No. 201010261392.9, dated Nov. 23, 2011.
Choi, S. W. et al., "Antioxidant and Antimelanogenic Activities of Polyamine Conjugates from Corn Bran and Related Hydroxycinnamic Acids," J. Agric. Food Chem., 2007, vol. 55, pp. 3920-3925.
Lim, J.Y. et al., "Tyrosinase Inhibitory p-Coumaric Acid from Ginseng Leaves," Phytotherapy Research, 1999, vol. 13, pp. 371-375.
Ohta, S. et al., "Antioxidant hydroxycinnamic acid derivatives isolated from Brazilian bee pollen," Natural Product Research, Jul. 10, 2007, vol. 21, No. 8, pp. 726-732.
Zamble, A. et al., "N1,N5,N10-Tris(4-hydroxycinnamoyl)spermidines from *Microdesmis keayana* Roots," Chemistry & Biodiversity, 2006, vol. 3, pp. 982-989.
Hamana et al., "Distribution of unusual polyamines in aquatic plants and gramineous seeds," Can J Botany, 1994, vol. 72, pp. 1114-1120.
Japanese Office Action for Japanese Application No. 2010-177865 dated Jan. 8, 2013 with English translation.
Ma et al., "Inhibitory Effects on HIV-1 Protease of Tri-p-coumaroylspermidine from *Artemisia caruifolia* and Related Amides," Chem. Pharm. Bull., Jul. 2001, vol. 49, No. 7, pp. 915-917.

(Continued)

*Primary Examiner* — Lezah Roberts
*Assistant Examiner* — Nannette Holloman
(74) *Attorney, Agent, or Firm* — Birch, Stewart, Kolasch & Birch, LLP

(57) ABSTRACT

A composition used for skin whitening includes: an effective amount of spermidine derivative, wherein a structure of the spermidine derivative is shown as Structure (I):

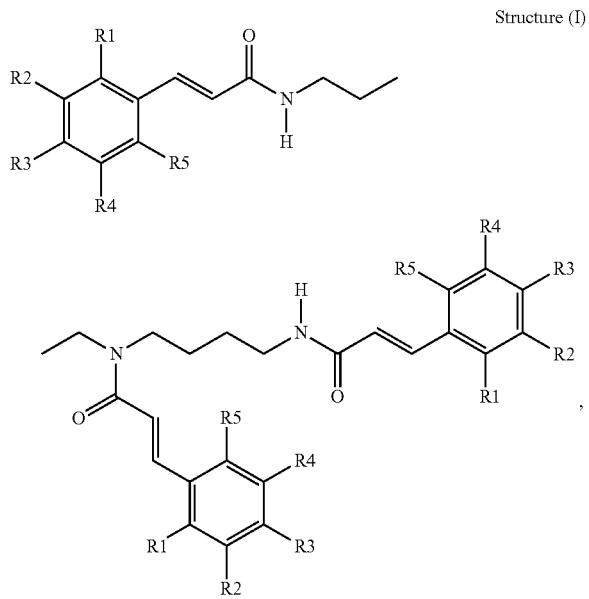

where R1-R5 individually includes H, OH, or $OCH_3$ and at least one of R1-R5 is OH, and the spermidine derivative has tyrosinase inhibition activity; and a cosmetically or pharmaceutically acceptable vehicle, wherein the composition used for skin whitening whitens skin.

16 Claims, No Drawings

(56) References Cited

OTHER PUBLICATIONS

Okombi et al., "Analogues of N-hydroxycinnamoylphenalkylamides as inhibitors of human melanocyte-tyrosinase," Bioorganic & Medicinal Chemistry Letters, 2006, No. 16, pp. 2252-2255.

Taiwanese Office Action of Taiwanese Application No. 099125868 dated Feb. 8, 2013.

Werner et al., "Di-Coumaroylspermidines and Tri-Coumaroylspermidines in Anthers of Different Species of the Genus Aphelandra," Phytochemistry, 1995, vol. 40, No. 2, pp. 461-465.

Japanese Office Action for Japanese Application No. 2010-177865, dated Jun. 18, 2013 with English translation.

Taiwanese Office Action, dated Sep. 23, 2013, for Application No. 099125868.

* cited by examiner

COMPOSITION USED FOR SKIN WHITENING, PLANT EXTRACTED SKIN WHITENING COMPOSITION AND COMPOSITION HAVING A SKIN WHITENING EFFECT

CROSS REFERENCE TO RELATED APPLICATIONS

This Application claims priority of Taiwan Patent Application No. 098126506, filed on Aug. 6, 2009, the entirety of which is incorporated by reference herein.

BACKGROUND OF THE INVENTION

1. Field of the Invention

The present invention is related to a composition used for skin whitening, and in particular relates to a plant extracted skin whitening composition containing a spermidine derivative, wherein the spermidine derivative has tyrosinase inhibition activity and may be applied to whiten skin.

2. Description of the Related Art

Due to tyrosinase catalysis, tyrosine which is contained in melanocytes originally, is converted to L-dopa and then L-dopa is converted to L-dopaquinone. After that, L-dopaquinone is subjected to serials of oxidations to form melanin, which is caused the darkening of skin. Tyrosinase is the key enzyme in the synthesis reaction of melanin, and thus the two oxidation processes, tyrosine converting to L-dopa and L-dopa converting to L-dopaquinone, may be slowed if tyrosinase is inhibited. Therefore, melanin synthesis may be reduced by inhibiting tyrosinase in melanocytes to reach the skin whitening effect.

The compounds, which are contained hydroquinone, ellagic acid, kojic acid, arbutin, glycopeptides and azelaic acid, etc., are well known to be used as inhibiting the synthesis of melanin.

Lian also called an entire plant of *Nelumbo Nucifer* Gaertn is a plant belonging to the Nymphaeaceae family. Chemical composition of *Nelumbo Nucifer* Gaertn has been reported such as anonaine, asimilobine, dehydronuciferine, dehydroroemerine, dehydroanonaine, demethylcoclaurine, liensinine, isoliensinine, etc. This invention finds a keayanidine compound of the spermidine derivatives as a skin whitening ingredient by using the bioactivity-guided fraction.

BRIEF SUMMARY OF THE INVENTION

The invention provides a composition used as skin whitening comprising: an effective amount of a spermidine derivative, wherein a structure of the spermidine derivative is shown as Structure (I):

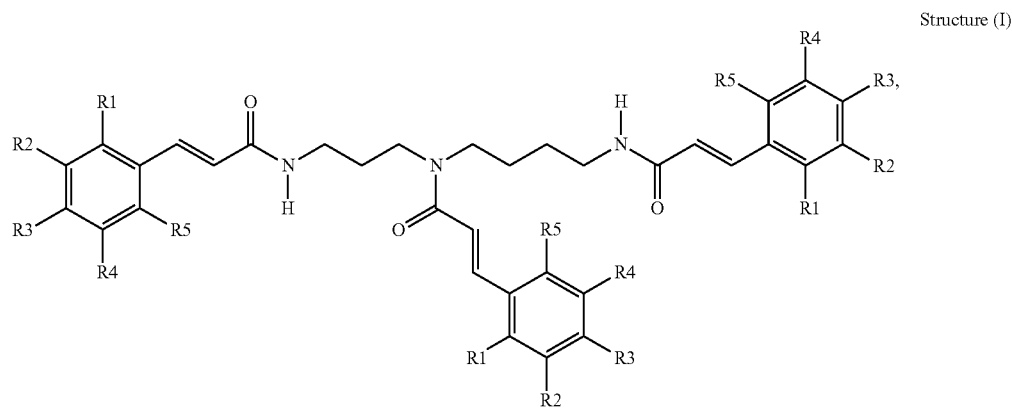

Structure (I)

where R1-R5 individually comprises H, OH, or $OCH_3$ and at least one of R1-R5 is OH, and the spermidine derivative has tyrosinase inhibition activity; and a cosmetically or pharmaceutically acceptable vehicle, wherein the composition used for skin whitening whitens skin.

The invention further provides a plant extracted skin whitening composition, comprising: an effective amount of a spermidine derivative extracted from a plant material, wherein a structure of the spermidine derivative is shown as Structure (I):

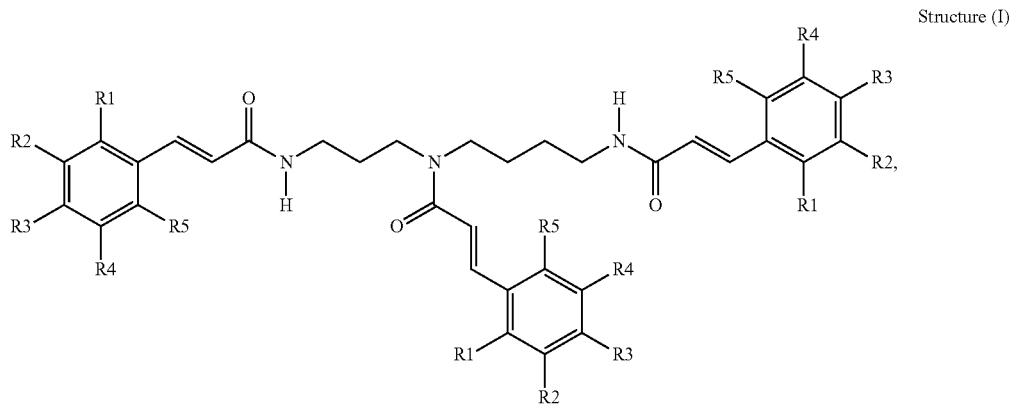

Structure (I)

where R1-R5 individually comprises H, OH, or OCH$_3$ and at least one of R1-R5 is OH, and the spermidine derivative has tyrosinase inhibition activity; and a cosmetically or pharmaceutically acceptable vehicle, wherein the plant extracted whiting skin composition is used as skin whitening.

The invention also provides a composition having a skin whitening effect comprising: an effective amount of a extract of a bud of a *Nelumbo Nucifer* Gaertn having tyrosinase inhibition activity, which comprises a spermidine derivative as an active ingredient, wherein a structure of the spermidine derivative is shown as Structure (I):

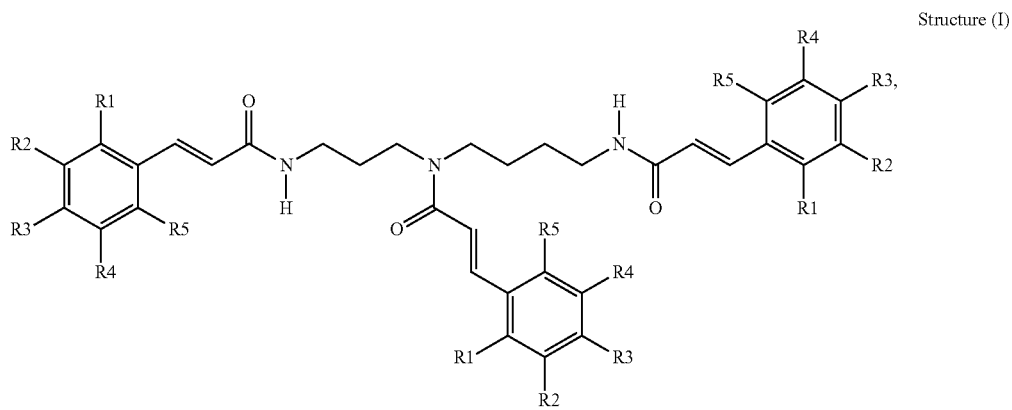

Structure (I)

where R1-R5 individually comprises H, OH, or OCH$_3$ and at least one of R1-R5 is OH, and the spermidine derivative has tyrosinase inhibition activity; and a cosmetically or pharmaceutically acceptable vehicle.

A detailed description is given in the following embodiments with reference to the accompanying drawings.

BRIEF DESCRIPTION OF THE DRAWINGS none

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

In the invention, a composition containing a spermidine derivative is applied to a skin whitening composition, which inhibits tyrosinase and whitens skin.

The composition mentioned above may comprise an effective amount of a spermidine derivative and a cosmetically or pharmaceutically acceptable vehicle, wherein the spermidine derivative has tyrosinase inhibition activity. A structure of the spermidine derivative mentioned above is shown as Structure (I):

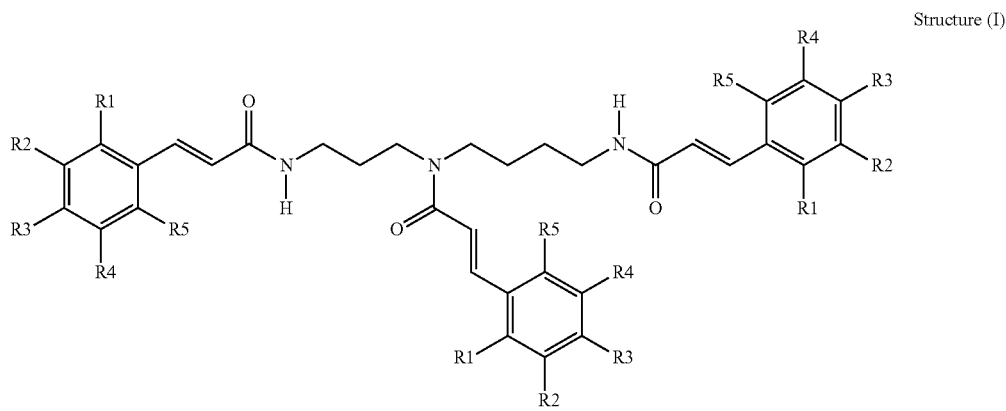

Structure (I)

In Structure (I), R1-R5 may individually comprise H, OH, or $OCH_3$ and at least one of R1-R5 is OH. In one embodiment, R3 is OH. In one embodiment, R1, R2, R4 and R5 of the spermidine derivative are H, respectively and R3 is OH. In another embodiment, R1, R2, R5 of the spermidine derivative are H, respectively, R3 is OH and R4 is $OCH_3$. In further another embodiment, R2, R3, R4 and R5 of the spermidine derivative are H, respectively and R1 is OH. In further another embodiment, R1, R2 and R5 of the spermidine derivative are H, respectively and R3 and R4 are OH, respectively.

The spermidine derivative may be extracted from a plant material. The plant material may comprise a bud of a *Nelumbo Nucifer* Gaertn, *Arachis hypogaea*, *Artemisia caruifolia*, *Quercus dentate*, Rosaceae, Acanthaceae or Pandaceae. In one embodiment, the plant material may comprise a bud of a *Nelumbo Nucifer* Gaertn.

A method for extracting the spermidine derivative from a plant material may comprise an appropriate solvent being used to perform an extraction process to the plant material. In one embodiment, acetone is used to perform the extraction process to the plant material. In other embodiment, after the plant material is extracted with acetone, other solvents may be used for further extraction. Other solvents may comprise n-hexane, ethyl ether, dichloromethane and/or ethyl acetate.

50% tyrosinase inhibitory concentration ($IC_{50}$) of the spermidine derivative mentioned above may be least less than about 450 μg/ml. In one embodiment, 50% tyrosinase inhibitory concentration ($IC_{50}$) of the spermidine derivative may be least less than about 37 μg/ml. In another embodiment, 50% tyrosinase inhibitory concentration ($IC_{50}$) of the spermidine derivative may be least less than about 19 μg/ml.

A tyrosinase inhibiting rate of the spermidine derivative with a concentration of 100 μg/ml may be at least greater than about 10%. In one embodiment, a tyrosinase inhibiting rate of the spermidine derivative with a concentration of 100 μg/ml may be about 10-65%.

In one embodiment, a structure of the spermidine derivative mentioned above is shown as Structure (II):

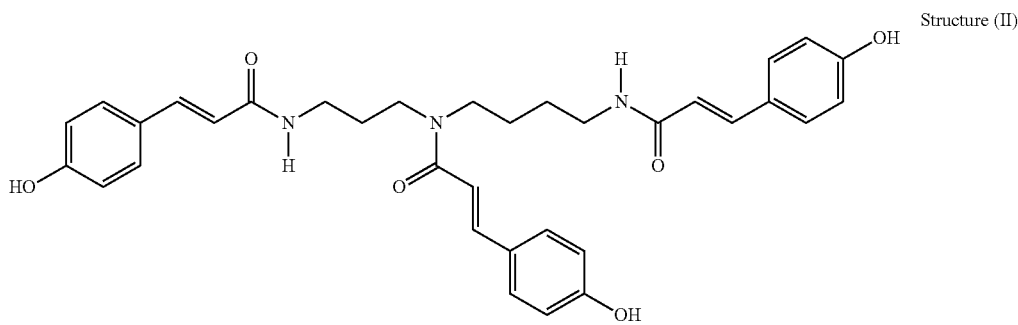 [SMILES: O=C(/C=C/c1ccc(O)cc1)NCCCCN(CCCNC(=O)/C=C/c1ccc(O)cc1)C(=O)/C=C/c1ccc(O)cc1]

Structure (II)

The spermidine derivative of Structure (II) may be extracted from a plant material. The plant material may comprise a bud of a *Nelumbo Nucifer* Gaertn, *Arachis hypogaea*, *Artemisia caruifolia*, *Quercus dentate*, Rosaceae, Acanthaceae or Pandaceae. In one embodiment, the plant material may comprise a bud of a *Nelumbo Nucifer* Gaertn.

50% tyrosinase inhibitory concentration ($IC_{50}$) of the spermidine derivative mentioned above may be least less than about 37 μg/ml and a tyrosinase inhibiting rate of the spermidine derivative with a concentration of 100 μg/ml may be about 62%.

In another embodiment, a structure of the spermidine derivative mentioned above is shown as Structure (III):

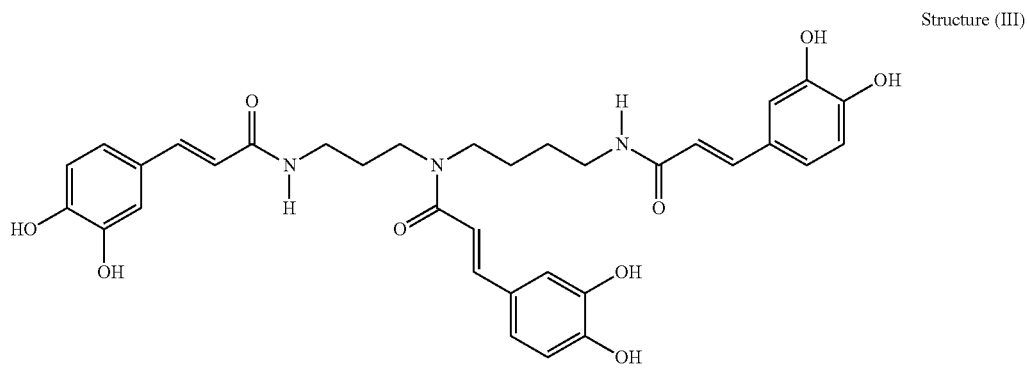 [SMILES: O=C(/C=C/c1ccc(O)c(O)c1)NCCCCN(CCCNC(=O)/C=C/c1ccc(O)c(O)c1)C(=O)/C=C/c1ccc(O)c(O)c1]

Structure (III)

50% tyrosinase inhibitory concentration (IC$_{50}$) of the spermidine derivative mentioned above may be least less than about 19 μg/ml and a tyrosinase inhibiting rate of the spermidine derivative with a concentration of 100 μg/ml may be about 63%.

In another aspect, the invention comprises a plant extracted skin whitening composition. The plant extracted skin whitening composition may comprise an effective amount of a spermidine derivative extracted from a plant material and a cosmetically or pharmaceutically acceptable vehicle, wherein the plant extracted skin whitening composition is used for skin whiting. A structure of the spermidine derivative is shown as Structure (I):

daceae. In one embodiment, the plant material may comprise a bud of a *Nelumbo Nucifer* Gaertn.

A method for extracting the spermidine derivative mentioned above from a plant material may comprise an appropriate solvent being used to perform an extraction process to the plant material. In one embodiment, acetone is used to perform the extraction process to the plant material. In other embodiment, after the plant material is extracted with acetone, other solvents may be used for further extraction. Other solvents may comprise n-hexane, ethyl ether, dichloromethane and/or ethyl acetate.

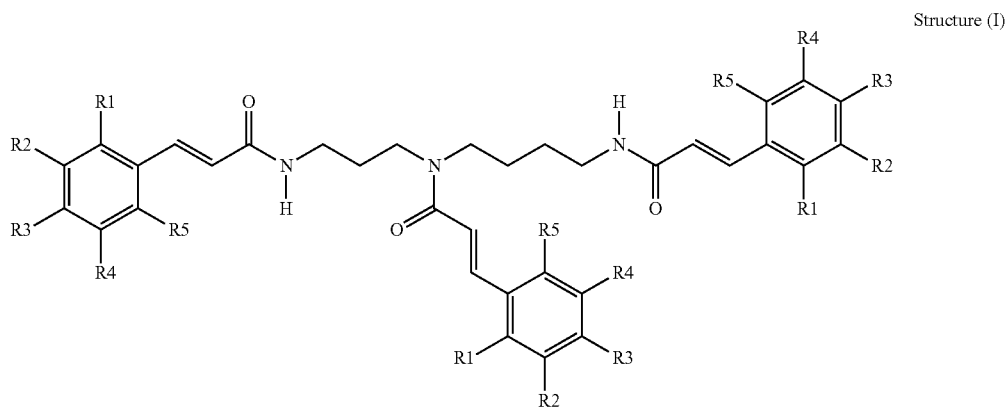

Structure (I)

In Structure (I), R1-R5 may individually comprise H, OH, or OCH$_3$ and at least one of R1-R5 is OH. In one embodiment, R3 is OH. In one embodiment, R1, R2, R4 and R5 of the spermidine derivative are H, respectively and R3 is OH. In another embodiment, R1, R2, R5 of the spermidine derivative are H, respectively, R3 is OH and R4 is OCH$_3$. In further another embodiment, R2, R3, R4 and R5 of the spermidine derivative are H, respectively and R1 is OH. In further another embodiment, R1, R2 and R5 of the spermidine derivative are H, respectively and R3 and R4 are OH, respectively.

The plant material mentioned above may comprise a bud of a *Nelumbo Nucifer* Gaertn, *Arachis hypogaea*, *Artemisia caruifolia*, *Quercus dentate*, Rosaceae, Acanthaceae or Pan- 50% tyrosinase inhibitory concentration (IC$_{50}$) of the spermidine derivative mentioned above may be least less than about 450 μg/ml. In one embodiment, 50% tyrosinase inhibitory concentration (IC$_{50}$) of the spermidine derivative may be least less than about 19 μg/ml. In addition, a tyrosinase inhibiting rate of the spermidine derivative with a concentration of 100 μg/ml may be at least greater than about 10%. In one embodiment, a tyrosinase inhibiting rate of the spermidine derivative with a concentration of 100 μg/ml may be about 10-65%.

In one embodiment, a structure of the spermidine derivative mentioned above is shown as Structure (II):

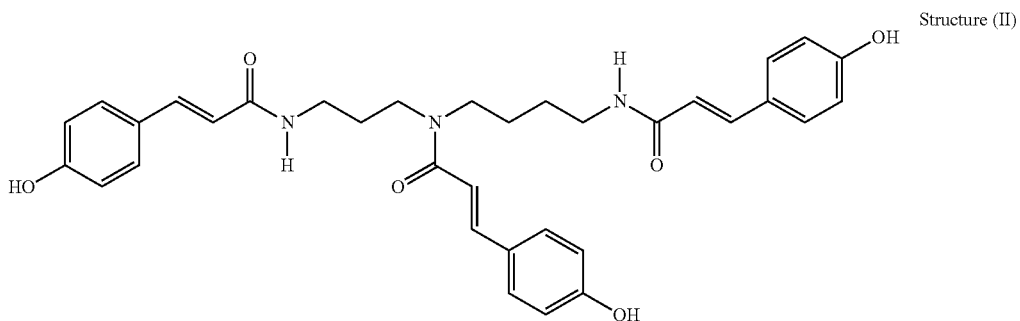 [SMILES: O=C(/C=C/c1ccc(O)cc1)NCCCCN(CCCNC(=O)/C=C/c1ccc(O)cc1)C(=O)/C=C/c1ccc(O)cc1]

Structure (II)

The plant material which may be extracted the spermidine derivative of Structure (II) out may comprise a bud of a *Nelumbo Nucifer* Gaertn, *Arachis hypogaea, Artemisia caruifolia, Quercus dentate*, Rosaceae, Acanthaceae or Pandaceae. In one preferable embodiment, the plant material may comprise a bud of a *Nelumbo Nucifer* Gaertn.

50% tyrosinase inhibitory concentration ($IC_{50}$) of the spermidine derivative of Structure (II) may be least less than about 37 μg/ml and a tyrosinase inhibiting rate of the spermidine derivative with a concentration of 100 μg/ml may be about 62%.

In further another aspect, the invention provides a composition having a skin whitening effect which may comprise an effective amount of an extract of a bud of a *Nelumbo Nucifer* Gaertn and a cosmetically or pharmaceutically acceptable vehicle.

The extract of a bud of a *Nelumbo Nucifer* Gaertn has tyrosinase inhibition activity. A method for forming the extract of a bud of a *Nelumbo Nucifer* Gaertn may comprise an appropriate solvent being used to perform an extraction process to the bud of a *Nelumbo Nucifer* Gaertn. In one embodiment, acetone is used to perform the extraction process to the bud of a *Nelumbo Nucifer* Gaertn to obtain the extract of a bud of a *Nelumbo Nucifer* Gaertn. In other embodiment, after the bud of a *Nelumbo Nucifer* Gaertn is extracted with acetone, other solvents may be used for further extracting to the extract of a bud of a *Nelumbo Nucifer* Gaertn. Other solvent may comprise n-hexane, ethyl ether, dichloromethane and/or ethyl acetate.

The extraction to the bud of a *Nelumbo Nucifer* Gaertn may comprise a spermidine derivative as an active ingredient, and a structure of the spermidine derivative is shown as Structure (I):

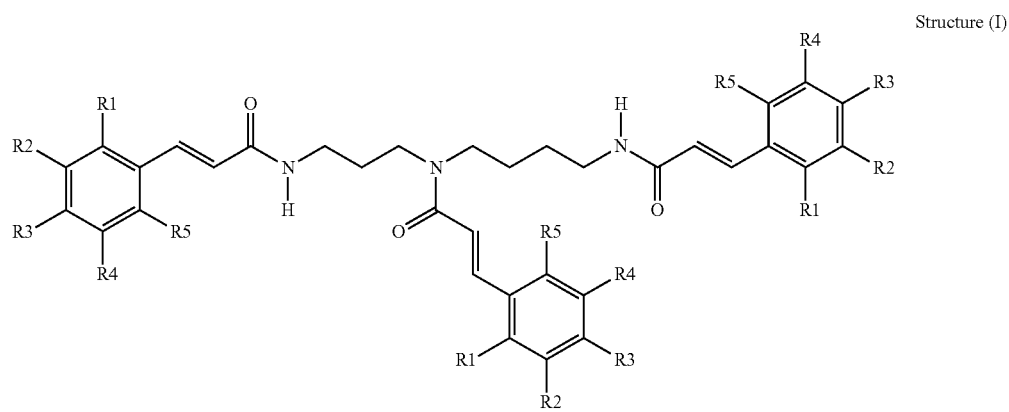

Structure (I)

In Structure (I), R1-R5 may individually comprise H, OH, or $OCH_3$ and at least one of R1-R5 is OH. In one embodiment, R3 is OH. In one embodiment, R1, R2, R4 and R5 of the spermidine derivative are H, respectively and R3 is OH. In another embodiment, R1, R2, R5 of the spermidine derivative are H, respectively, R3 is OH and R4 is $OCH_3$. In further another embodiment, R2, R3, R4 and R5 of the spermidine derivative are H, respectively and R1 is OH. In further another embodiment, R1, R2 and R5 of the spermidine derivative are H, respectively and R3 and R4 are OH, respectively.

50% tyrosinase inhibitory concentration ($IC_{50}$) of the spermidine derivative mentioned above may be least less than about 450 µg/ml. In one embodiment, 50% tyrosinase inhibitory concentration ($IC_{50}$) of the spermidine derivative may be least less than about 19 µg/ml. In addition, a tyrosinase inhibiting rate of the spermidine derivative with a concentration of 100 µg/ml may be at least greater than about 10%. In one embodiment, a tyrosinase inhibiting rate of the spermidine derivative with a concentration of 100 µg/ml may be about 10-65%.

In one embodiment, a structure of the spermidine derivative mentioned above is shown as Structure (II):

agents may be also included in the compositions mentioned above. The vehicle may also further include adjuncts such as antioxidants, perfumes, opacifiers, preservatives, colourants and buffers.

Furthermore, in one embodiment, all of the compositions mentioned may be manufactured as a skin spreading form, including, but not limited to creams, ointments, gels, sprays, lotions, skin tonics, shampoos or mousses, etc. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. A skin mousse is foam released under pressure from an aerosolized can. Skin creams may be a hydrophobic or hydrophilic cream, ointment, gel, emollient, spray, lotion, skin tonic, shampoo or mousse, suitably with additional ingredients suitable for use in skin cream of types known in the art, and such further ingredients can include

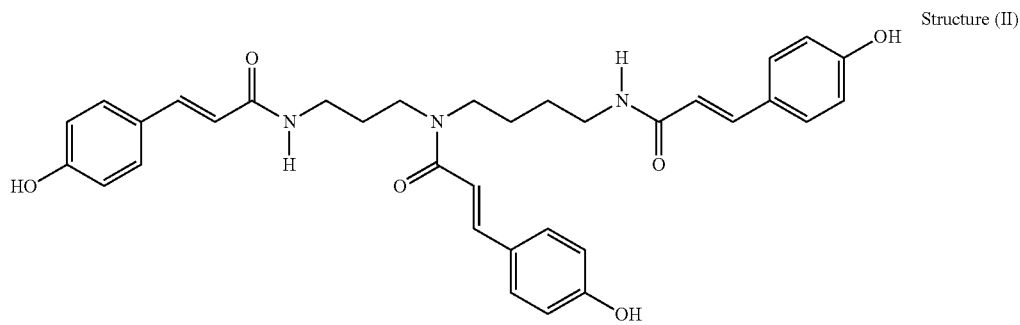 [SMILES: O=C(/C=C/c1ccc(O)cc1)NCCCCN(CCCNC(=O)/C=C/c1ccc(O)cc1)C(=O)/C=C/c1ccc(O)cc1]

Structure (II)

50% tyrosinase inhibitory concentration ($IC_{50}$) of the spermidine derivative of Structure (II) may be least less than about 37 µg/ml and a tyrosinase inhibiting rate of the spermidine derivative with a concentration of 100 µg/ml may be about 62%.

Furthermore, the cosmetically or pharmaceutically acceptable vehicles for all compositions mentioned above may act as a dilutent, dispersant or carrier for the active ingredient. The cosmetically or pharmaceutically acceptable vehicle may comprise materials commonly employed in skin care products such as water, liquid or solid emollients, silicone oils, emulsifiers, solvents, humectants, thickeners, powders, propellants and the like.

The vehicle may be formed from 5%-99.9 wt %, preferably from 25-80% by weight of the compositions mentioned above, and can, in the absence of other adjuncts, form the balance of the compositions.

Moreover, other specific ingredients which benefit skin, such as sunscreens, skin-lightening agents, and skin tanning petrolatum, waxes, lanolin, silicone, liposomes, vegetable, mineral oils, plasticizers, fragrances, preservatives, a penetration enhancing agent, a pH adjusting agent or other suitable ingredients for skin creams. Such ingredients can moisturize skin, stabilize the active compound, increase the composition-skin contact, local concentration and control the composition release.

Example

The compounds 1-4 having the common structure shown in the following were obtained by plant extraction or synthesis. The structures of the compounds 1-4 are shown in Table 1, respectively.

TABLE 1

Structures of the compounds 1-4

Structure (I)

| Compound | R1-R5 |
|---|---|
| 1 | R3 = OH; R1, R2, R4, R5 = H |
| 2 | R3 = OH; R4 = OCH₃; R1, R2, R5 = H |
| 3 | R1 = OH; R2, R3, R4, R5 = H |
| 4 | R3, R4 = OH; R1, R2, R5 = H |

In the examples of the invention, a tyrosinase inhibition test and melanin content test were used to perform the effect analysis and are described in the following, respectively.

Tyrosinase Inhibition Test (See Biol. Pharm. Bull. 25(8) 1045-1048 (2002); Biol. Pharm. Bull. 27(12) 1976-1978 (2004))

1. A tyrosinase solution using Tyrosinase (Sigma T3824) was prepared, wherein after diluted with a 0.1 M phosphate buffer, a 0.1 U/µl tyrosinase solution was obtained.

2. A L-Dopa solution using L-Dopa (Sigma D9628) was prepared, wherein after diluted with a 0.1 M phosphate buffer, a 1 mM L-Dopa solution was obtained and then was placed a dark environment.

3. A test sample solution was prepared comprising 10 mg/ml of a sample solution diluted with 100% of DMSO. Then the test sample solution was further diluted for require concentrations using a 0.1 M phosphate buffer.

4. 50 µl/well of the prepared test sample solution mentioned above was added into the wells of a 96 well plate (note that the same diluted concentration of DMSO for the test sample solution was also added into the wells of a 96 well plate and used for the blank group) and then 90 µl/well of the prepared 0.1 U/µl tyrosinase solution mentioned above was added thereto (the dC control group was added the 0.1 M phosphate buffer but not the 0.1 U/µl tyrosinase solution). The 96 well plate was placed under a temperature of 37° C. and mixed at 450 rpm for 5 minutes and then placed in an ELISA reader (Molecular Devices M2). The wave length of the ELISA reader was set at 492 nm to determine absorbance values of the solutions in the 96 well plate, wherein two absorbance values were determined and the average value therefrom was used as a background value. Next, 60 µl/well of the prepared 1 mM L-Dopa solution mentioned above was added to the 96 well plate (the dD control group was added the 0.1 M phosphate buffer not the 1 mM L-Dopa solution) and then the 96 well plate was placed under a temperature of 37° C. in a dark environment and mixed at 450 rpm for 15 minutes and then placed in a ELISA reader (Molecular Devices M2). The wave length of the ELISA reader was set at 492 nm to determine absorbance values of the solutions in the 96 well plate, wherein two absorbance values were determined and the average value therefrom was used as a measurement value. After the background value was subtracted from the measurement value, the tyrosinase inhibiting rate of the sample was calculated. The formula for calculating the tyrosinase inhibiting rate of the sample is shown in the following:

$$(A-A_0)-(B-B_0)-dC-dD/(A-A_0)\times 100\%$$

A: absorbance value of the blank group

B: absorbance value of the sample $A_0$: background value of the blank group $B_0$: background value of the sample dC: absorbance variation for the sample only reacted with the L-Dopa dD: absorbance variation for the sample only reacted with the tyrosinase Melanin Inhibition Test 1. Cell Line Culturing Mouse melanoma B16-F0 (ATCC CRL-6322, bought from Food Industry Research and Development Institute (FIRDI) (331 Shih-Pin Road, Hsinchu, 300 Taiwan R.O.C.)) was cultured in a medium (Dulbecco's MEM, DMEM) containing 10% fetal bovine serum and 1% penicillin-streptomycin under a temperature of 37° C., in a 5% $CO_2$ incubator.

2. Melanin Content Analysis

Inhibition of B16 Cell Melanin by Extracts:

After a test sample was added to the B16 cells in the medium for 48 hours, the medium was removed. The B16 cells were washed twice with the PBS buffer and then 300 µl of a 1N NaOH which was preheated at a temperature of 70° C. was added to the B16 cells and the B16 cells were, placed in a 60° C. incubator for 60 minutes. Next, 200 µl of the 1N NaOH which had been added to the B16 cells mention above was added to a 96 well plate to determined the absorbance value at 405 nm. The formula for calculating the melanin content is shown in the following:

$$\text{Melanin content}=(M/M_0)\times 100\%$$

M: absorbance value for B16 cells being treated with sample $M_0$: absorbance value for B16 cells not being treated with sample

Example 1

Extracting and Purifying Compound 1 from a Plant Material

Buds of a *Nelumbo Nucifer* Gaertn were extracted with acetone to form an extract. Next, 4.5 g of the extract was dissolved and mixed in 22.5 ml of methanol and water, to form a mixed solution. The mixed solution was extracted 3 times with 22.5 ml of n-hexane, ethyl ether, dichloromethane and ethyl acetate, respectively to form an n-hexane layer extract solution, ethyl ether layer extract solution, dichloromethane layer extract solution and ethyl acetate layer extract solution, respectively. After each layer extract solution was concentrated and dried, each layer extract was formed and the tyrosinase inhibition test was performed thereto.

The results showed that the ethyl acetate layer extract had tyrosinase inhibition activity.

After the ethyl acetate layer extract solution was concentrated and dried, 1.7883 g of the ethyl acetate layer extract was obtained. The tyrosinase inhibition rate of the ethyl acetate layer extract was 86.98±2.6%

Then, 1.5 g of the ethyl acetate layer extract was isolated by a reversed phase open chromatographic column (filled with 37.5 g of a RP-18 silica gel, 2×33 cm). The mobile phase change of the column comprised methanol:water=1:10→1:8→1:4→1:2→1:1→methanol. After the ethyl acetate layer extract was isolated by column chromatography, 0.0875 g of a compound was obtained. Spectral analysis and mass spectrometry analysis were performed on the compound. The results are shown in the following.

Spectral Analysis:

$^1$HNMR (500 MHz, CD3OD): 7.56-7.34 (m, 9H); 6.88-6.72 (m, 7H), 6.44-6.35 (m, 2H); 3.57-3.47 (m, 4H); 3.36-3.31 (m, 4H); 1.94-1.84 (m, 2H); 1.74-1.58 (m, 4H).

Mass Spectrometry Analysis

ESI$^+$-MS: 606[M+Na]$^+$; 438; 204

According the results of the spectral analysis and mass spectrometry analysis, it showed that the compound was compound 1.

Next, a tyrosinase inhibition test and 50% tyrosinase inhibitory concentration (IC$_{50}$) calculation were performed to compound 1 and the results are shown in Table 2. The results showed that the a tyrosinase inhibiting rate of compound 1 with a concentration of 100 μg/ml was about 61.2±2.5%. Also, 50% tyrosinase inhibitory concentration (IC$_{50}$) of compound 1 was 36.2±2.5 μg/ml. Moreover, a melanin content test was performed to compound 1 to show the effects of the compound to the melanin content of cells. The test result showed that a melanin content inhibiting rate of compound 1 with a concentration of 100 μg/ml was about 19.9±4.2%.

Example 2

Synthesis of Compound 2

0.44 g of ferulic acid, 0.1 g of spermidine, 0.33 g of 1-hydroxybenzotriazole and 0.476 g of N,N'-dicyclohexylcarbodiimide (DCC) were in 15 ml of tetrahydrofuran to react at room temperature for 16 hours. Next, tetrahydrofuran was removed from the reacted solution by a rotary evaporator to form a substance, and then methanol was added to the substance, stirred and filtered to remove insoluble solids. The filtered methanol was evaporated to obtain 1.2509 g of a resultant product. 0.12 g of the resultant product was dissolved in 1 ml of methanol and the insoluble portions of the resultant product was removed by filtering. The filtered methanol was isolated by a semi-preparative reversed phase chromatographic column (mobile phase comprised water and acetonitrile) and collected to obtain 3.4 mg of a compound. Spectral analysis was performed on the compound. The result is shown in the following.

$^1$HNMR (500 MHz, CD3OD): 7.79-7.69 (m, 2H); 7.55-7.34 (m, 4H); 7.21-6.72 (m, 7H); 6.47-6.37 (m, 2H); 3.92-3.86 (m, 9H); 3.62-3.45 (m, 4H); 3.38-3.34 (m, 4H); 1.95-1.85 (m, 2H); 1.74-1.60 (m, 4H).

According the result of the spectral analysis, it showed that the compound was compound 2.

Tyrosinase Inhibition Test

A tyrosinase inhibition test and 50% tyrosinase inhibitory concentration (IC$_{50}$) calculation were performed to compound 2 and the results are shown in Table 2. The results showed that a tyrosinase inhibiting rate of compound 2 with a concentration of 100 μg/ml was 15.0±1.7% and a tyrosinase inhibiting rate of compound 2 with a concentration of 125 μg/ml was 29.2±2.0%. 50% tyrosinase inhibitory concentration (IC$_{50}$) of compound 2 was 225.4±15.6

Example 3

Synthesis of Compound 3

0.37 g of 2-hydroxy cinnamic acid, 0.1 g of spermidine, 0.33 g of 1-hydroxybenzotriazole and 0.5 g of N,N'-dicyclohexylcarbodiimide (DCC) were in 10 ml of tetrahydrofuran to react at room temperature for 16 hours. Next, tetrahydrofuran was removed from the reacted solution by a rotary evaporator to form a reacted substance, and then methanol was added to the reacted substance, stirred and filtered to remove insoluble solids. The filtered methanol was evaporated to obtain 0.2546 g of a resultant product. 0.06 g of the resultant product was dissolved in 1 ml of methanol and the insoluble portions of the resultant product was removed by filtering. The filtered methanol was isolated by a semi-preparative reversed phase chromatographic column (mobile phase comprised water and acetonitrile) and collected to obtain 2.2 mg of a compound. Spectral analysis was performed on the compound. The result is shown in the following.

$^1$HNMR (500 MHz, CD3OD): 7.84-7.80 (m, 2H); 7.49 (t, 1H); 7.48-7.43 (m, 3H); 7.28-7.09 (m, 4H); 6.83-6.69 (m, 8H); 3.57-3.49 (m, 4H); 3.45-3.31 (m, 4H); 1.96-1.88 (m, 2H); 1.67-1.61 (m, 4H).

According the result of the spectral analysis, it showed that the compound was compound 3.

Tyrosinase Inhibition Test

A tyrosinase inhibition test and 50% tyrosinase inhibitory concentration (IC$_{50}$) calculation were performed to compound 3 and the results are shown in Table 2. The results showed that a tyrosinase inhibiting rate of compound 3 with a concentration of 100 μg/ml was 10.4±0.1% and a tyrosinase inhibiting rate of compound 3 with a concentration of 125 μg/ml was 13.2±1.1%. 50% tyrosinase inhibitory concentration (IC$_{50}$) of compound 3 was 438.7±77.4 μg/ml.

Example 4

Synthesis of Compound 4

10 g of caffeic acid were dissolved in 120 ml of tetrahydrofuran to form a solution, and then the solution was placed in an ice bath, 24 ml of triethylamine and 12 ml of acetyl chloride were added to the solution. After the solution was stirred for 22 hours, the solvent of the solution was removed by a rotary evaporator. The reacted substance was added to 200 ml of dichloromethane to be dissolved, washed with 100 ml of water for three times and dried by magnesium sulfate, and then the remaining solvent was removed by a rotary evaporator to obtain 13.481 g of a product.

5.251 g of the product was added to 47 ml of methanol, heated and dissolved to form a solution. After the solution was cooled, the solution was placed in a refrigerator for three days, and then a solid separated out from the solution was filtered, washed with a small amount of methanol and dried to obtain 0.87 g of a purified product.

0.25 g of the purified product and 2 ml of $SOCl_2$ were dissolved in dry tetrahydrofuran to react at room temperature for 23 hours to form a mixture, and the solvent and excess $SOCl_2$ of the mixture were removed by a rotary evaporator. The reacted substance was dissolved in 10 ml of tetrahydrofuran, which was dropped slowly into a reactive bottle containing 0.042 g of spermidine, 0.133 ml of triethylamine and 10 ml of tetrahydrofuran in an ice bath, then the reacted solution was refluxed for 4 hours. After the reaction was completed, tetrahydrofuran in the reacted solution was removed by a rotary evaporator, and the reacted substance was added 20 ml of dichloromethane to be dissolved and washed with 10 ml of water for three times, and then the dichloromethane layer was dried by magnesium sulfate and concentrated by a rotary evaporator to obtain 0.2826 g of an acetylated product.

0.1 g of the acetylated product, 1 ml of tetrahydrofuran, 1 ml of methanol and 0.6 ml of concentrated hydrochloric acid were reacted at 60° C. for 30 minutes to form a reacted solution. Next, 10 ml of water and 10 ml of dichloromethane were added to the reacted solution and then an insoluble substance was separated out. The insoluble substance was added to 1 ml of methanol to be dissolved, isolated by RP-18 thin layer chromatography (mobile phase comprised water and acetonitrile) and purified to obtain 6.4 mg of a compound 4. Spectral analysis and mass spectrometry analysis were performed on the compound. The results are shown in the following.

Spectral Analysis:

$^1$HNMR (500 MHz, CD3OD): 7.49-7.36 (m, 3H); 7.08-6.71 (m, 10H); 6.39-6.32 (m, 2H); 3.60-3.46 (m, 4H); 3.36-3.31 (m, 4H); 1.94-1.82 (m, 2H); 1.73-1.57 (m, 4H).

Mass Spectrometry Analysis

ESI$^+$-MS: 632[M+1]$^+$; 470

According the result of the spectral analysis and mass spectrometry analysis, it showed that the compound was compound 4.

Tyrosinase Inhibition Test

A tyrosinase inhibition test and 50% tyrosinase inhibitory concentration ($IC_{50}$) calculation were performed to compound 4 and the results are shown in Table 2. The results showed that a tyrosinase inhibiting rate of compound 4 with a concentration of 100 μg/ml was 62.2±27.2% and a tyrosinase inhibiting rate of compound 4 with a concentration of 125 μg/ml was 74.5±16.1%. 50% tyrosinase inhibitory concentration ($IC_{50}$) of compound 4 was 18.6±2.9 μg/ml.

TABLE 2

Tyrosinase inhibiting rates and 50% tyrosinase inhibitory concentration ($IC_{50}$) of compounds 1-4

| Compound | Purity (%) | Tyrosinase inhibiting rate (%) (100 μg/ml) | $IC_{50}$ (μg/ml) |
|---|---|---|---|
| 1 | 98.0 | 61.2 ± 2.5 | 36.2 ± 2.5 |
| 2 | 83.4 | 15.0 ± 1.7 | 225.4 ± 15.6 |
| 3 | 84.8 | 10.4 ± 0.1 | 438.7 ± 77.4 |
| 4 | 92 | 62.2 ± 27.2 | 18.6 ± 2.9 |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A composition used for skin whitening comprising:
an effective amount of a spermidine derivative as the only active ingredient, wherein a structure of the spermidine derivative is shown as Structure (I):

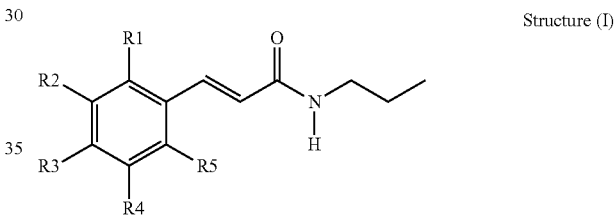

Structure (I)

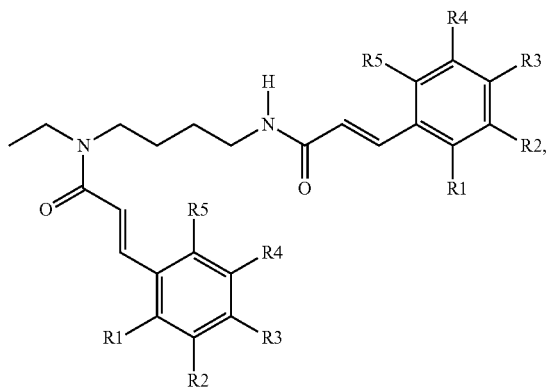

where R1-R5 individually comprises H, OH, or $OCH_3$ and at least one of R1-R5 is OH, and the spermidine derivative has tyrosinase inhibition activity; and
a cosmetically or pharmaceutically acceptable vehicle, wherein the composition used for skin whitening whitens skin.

2. The composition used for skin whitening as claimed in claim 1, wherein R3 of the spermidine derivative is OH.

3. The composition used for skin whitening as claimed in claim 1, wherein R1, R2, R4 and R5 of the spermidine derivative are H, respectively and R3 is OH, or wherein R1, R2, R5 of the spermidine derivative are H, respectively, R3 is OH and R4 is $OCH_3$ or wherein R2, R3, R4 and R5 of the spermidine derivative are H, respectively and R1 is OH or wherein R1, R2 and R5 of the spermidine derivative are H, respectively and R3 and R4 are OH, respectively.

4. The composition used for skin whitening as claimed in claim 1, wherein the spermidine derivative is extracted from a plant material.

5. The composition used for skin whitening as claimed in claim 4, wherein the plant material comprises a bud of a *Nelumbo Nucifer* Gaertn, *Arachis hypogaea, Artemisia caruifolia, Quercus dentate*, Rosaceae, Acanthaceae or Pandaceae.

6. The composition used for skin whitening as claimed in claim 1, wherein a tyrosinase inhibiting rate of the spermidine derivative with a concentration of 100 μg/ml is at least greater than about 10%.

7. The composition used for skin whitening as claimed in claim 1, wherein 50% tyrosinase inhibitory concentration ($IC_{50}$) of the spermidine derivative is at least less than about 450 μg/ml.

8. The composition used for skin whitening as claimed in claim 1, wherein a structure of the spermidine derivative is shown as Structure (II):

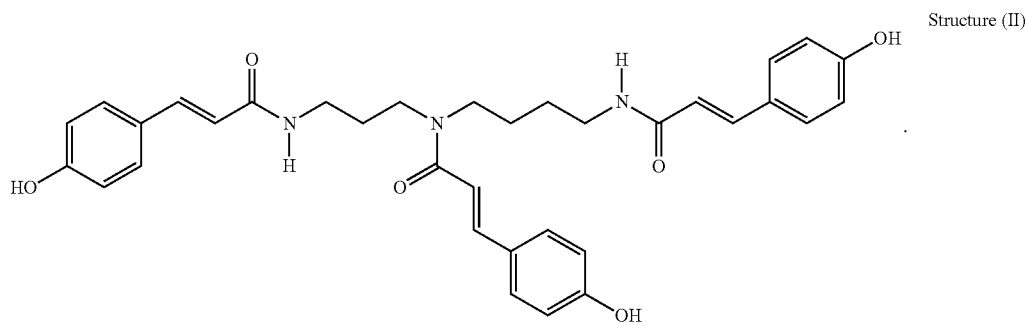 [SMILES: O=C(/C=C/c1ccc(O)cc1)NCCCCN(CCCNC(=O)/C=C/c1ccc(O)cc1)C(=O)/C=C/c1ccc(O)cc1]

Structure (II)

9. The composition used for skin whitening as claimed in claim 8, wherein the spermidine derivative is extracted from a plant material.

10. The composition used for skin whitening as claimed in claim 9, wherein the plant material comprises a bud of a *Nelumbo Nucifer* Gaertn, *Arachis hypogaea, Artemisia caruifolia, Quercus dentate*, Rosaceae, Acanthaceae or Pandaceae.

11. The composition used for skin whitening as claimed in claim 9, wherein the plant material comprises a bud of a *Nelumbo Nucifer* Gaertn.

12. The composition used for skin whitening as claimed in claim 8, wherein a tyrosinase inhibiting rate of the spermidine derivative with a concentration of 100 μg/ml is about 62%.

13. The composition used for skin whitening as claimed in claim 8, wherein 50% tyrosinase inhibitory concentration ($IC_{50}$) of the spermidine derivative is at least less than about 37 μg/ml.

14. The composition used for skin whitening as claimed in claim 1, wherein a structure of the spermidine derivative is shown as Structure (III):

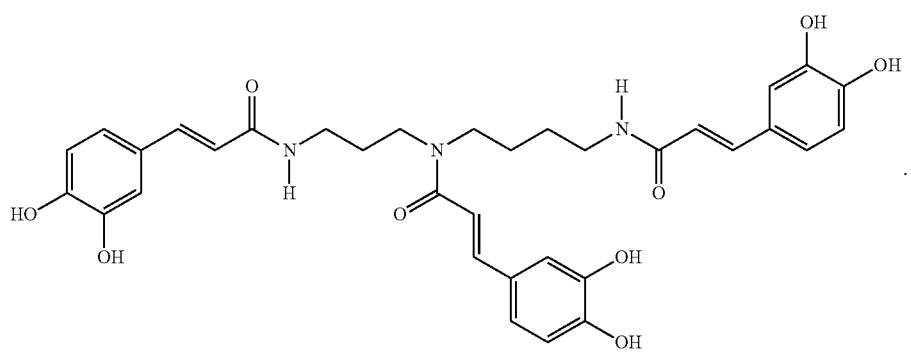
Structure (III)
15. The composition used for skin whitening as claimed in claim 14, wherein a tyrosinase inhibiting rate of the spermidine derivative with a concentration of 100 μg/ml is about 63%.
16. The composition used for skin whitening as claimed in claim 14, wherein 50% tyrosinase inhibitory concentration ($IC_{50}$) of the spermidine derivative is at least less than about 19 μg/ml.
* * * * *